(12) United States Patent
Gross et al.

(10) Patent No.: US 9,091,639 B2
(45) Date of Patent: Jul. 28, 2015

(54) METHOD FOR CALIBRATING AND/OR ADJUSTING AN ANALYTICAL DEVICE FOR CHEMICAL SUBSTANCES IN LIQUIDS, ESPECIALLY IN AQUEOUS SOLUTIONS

(75) Inventors: Andrea Gross, Leonberg (DE); Ulrich Kathe, Ludwigsburg (DE); Thomas Schipolowski, Stuttgart (DE); Ralf Steuerwald, Eberdingen (DE)

(73) Assignee: Endress + Hauser Conducta Gesellschaft für Mess-und Regeltechnik mbH + Co. KG, Gerlingen (DE)

( * ) Notice: Subject to any disclaimer, the term of this patent is extended or adjusted under 35 U.S.C. 154(b) by 0 days.

(21) Appl. No.: 13/611,386

(22) Filed: Sep. 12, 2012

(65) Prior Publication Data

US 2013/0084642 A1 Apr. 4, 2013

(30) Foreign Application Priority Data

Sep. 30, 2011 (DE) .......................... 10 2011 083 886
Nov. 23, 2011 (DE) .......................... 10 2011 086 942

(51) Int. Cl.
*G01N 21/78* (2006.01)
*G01N 21/27* (2006.01)

(52) U.S. Cl.
CPC .............. *G01N 21/274* (2013.01); *G01N 21/78* (2013.01); *G01N 21/272* (2013.01); *G01N 21/276* (2013.01); *G01N 21/278* (2013.01); *Y10T 436/10* (2015.01)

(58) Field of Classification Search
CPC ..... G01N 21/25; G01N 21/27; G01N 21/274; G01N 21/276; G01N 21/278; G01N 21/59; G01N 21/78; G01N 21/93; G01N 35/00584; G01N 35/00594; G01N 21/272; G01N 21/75; G01N 21/77; Y10T 436/10

USPC ............ 436/8, 43, 164, 166; 422/68.1, 82.05, 422/82.09; 73/1.01, 1.02, 1.03
See application file for complete search history.

(56) References Cited

U.S. PATENT DOCUMENTS

| | | | |
|---|---|---|---|
| 3,895,913 | A | 7/1975 | Bockowski |
| 4,024,021 | A | 5/1977 | Stavropoulos |

(Continued)

FOREIGN PATENT DOCUMENTS

| | | |
|---|---|---|
| CA | 2701301 | 7/2009 |
| DE | 10391021 B4 | 7/2007 |

(Continued)

OTHER PUBLICATIONS

German Search Rpt, Sep. 12, 2012, German Patent Office.

*Primary Examiner* — Maureen Wallenhorst
(74) *Attorney, Agent, or Firm* — Bacon & Thomas, PLLC

(57) ABSTRACT

The invention relates to a method for calibrating and/or adjusting an analytical device for chemical substances. A predetermined concentration of a chemical substance in a reference liquid is measured by mixing the reference liquid with a reagent for producing a color change, followed by irradiating with light of a predetermined wavelength. Based on the absorption of the light by the reference liquid, a concentration is determined, which is compared with the predetermined concentration of the reference liquid. In the case of which a calibrating and/or adjusting associated with the measurement process is possible without long interruptions of the measurement process, the predetermined concentration of the reference liquid is gained by mixing at least two standard, which contain different concentrations of the chemical substance.

14 Claims, 1 Drawing Sheet

(56) References Cited

U.S. PATENT DOCUMENTS

| | | | |
|---|---|---|---|
| 4,801,538 A | 1/1989 | Hanada | |
| 5,307,146 A | 4/1994 | Porter | |
| 5,576,219 A * | 11/1996 | Bienhaus et al. | 436/500 |
| 5,629,212 A * | 5/1997 | Herman et al. | 436/125 |
| 5,965,448 A | 10/1999 | Katou | |
| 5,989,916 A | 11/1999 | Purdie | |
| 7,105,354 B1 | 9/2006 | Shimoide | |
| 7,504,264 B2 | 3/2009 | Rhode | |
| 8,003,048 B2 * | 8/2011 | Clay et al. | 422/63 |
| 2006/0193747 A1 | 8/2006 | Saito | |
| 2006/0216830 A1 | 9/2006 | Kikuiri | |
| 2008/0261315 A1 | 10/2008 | Strongin | |
| 2011/0217762 A1 | 9/2011 | Viator | |

FOREIGN PATENT DOCUMENTS

| | | | |
|---|---|---|---|
| EP | 2264449 | * | 12/2010 |
| FR | 1443908 | | 5/1966 |
| FR | 2569008 A1 | | 2/1986 |
| WO | 2011137484 A1 | | 11/2011 |

* cited by examiner

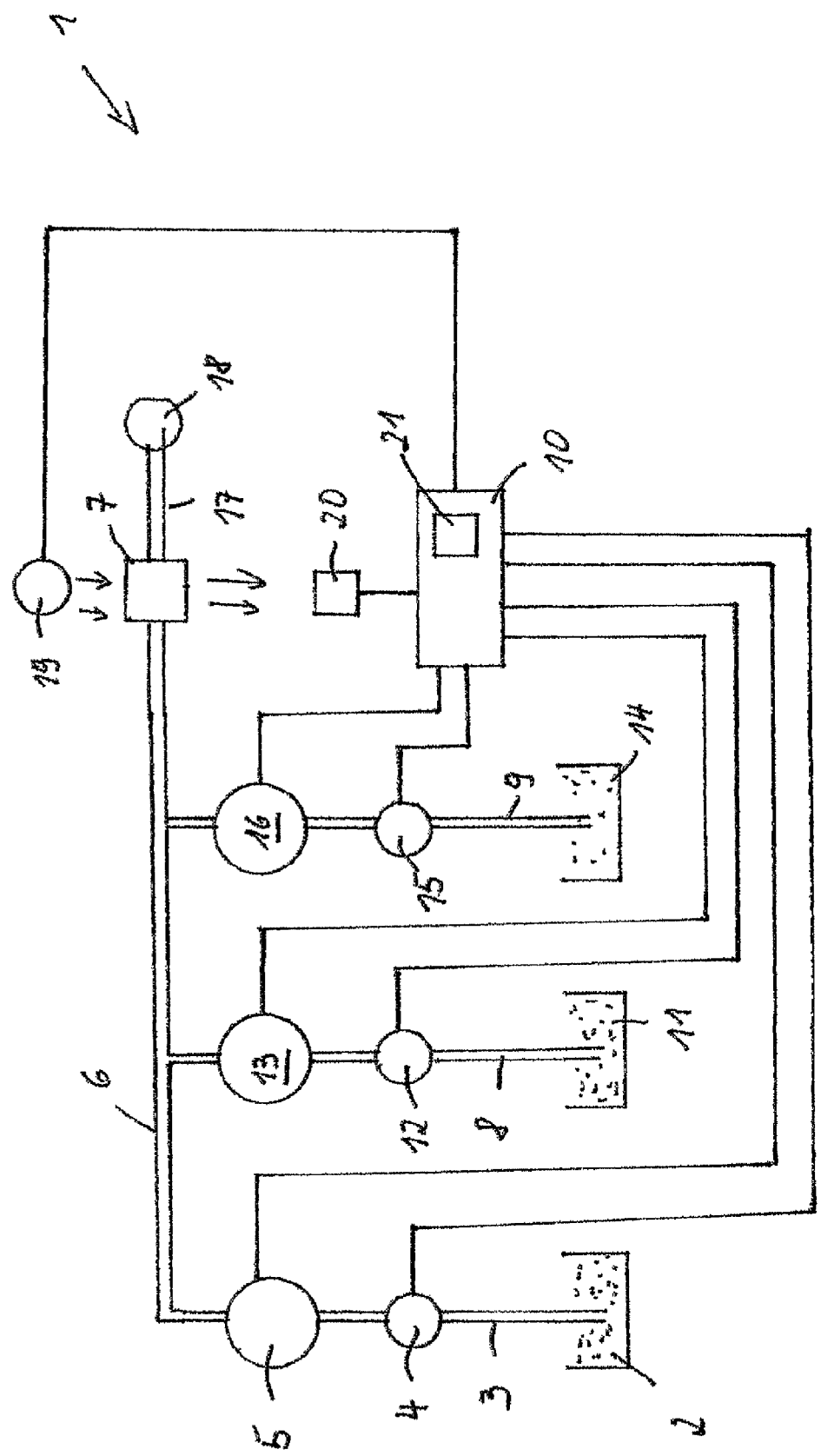

METHOD FOR CALIBRATING AND/OR ADJUSTING AN ANALYTICAL DEVICE FOR CHEMICAL SUBSTANCES IN LIQUIDS, ESPECIALLY IN AQUEOUS SOLUTIONS

TECHNICAL FIELD

The invention relates to a method for calibrating and/or adjusting an analytical device for chemical substances in liquids, especially in aqueous solutions, in the case of which a predetermined concentration of a chemical substance is measured in a reference liquid by mixing the reference liquid with a reagent for producing a color change, followed by irradiating with light of a predetermined wavelength; wherein, based on the absorption of the light by the reference liquid, a concentration is determined, which is compared with the predetermined concentration of the reference liquid.

BACKGROUND DISCUSSION

The present invention is concerned with process analytics, in the case of which a concentration of a chemical substance in water, especially in wastewater or drinking water, is examined. From DE 10 2004 015 387 A1, a method for photometric determination of the total hardness of aqueous solutions is known, in the case of which a reagent is mixed with a sample of an aqueous solution to be examined. The reagent causes, in such case, a color change of the solution to be examined, which is then subjected to a photometric measuring. By means of the measured absorption of the light, the hardness of the aqueous solution is determined.

EP 2 264 449 A1 likewise discloses a photometric method for quantitative determination of an analyte in water, in the case of which, in the process analytical procedure, the sample taking and the metering of the analyte occur, as a rule, fully automatically. In a process analysis device, a chemical substance in water is automatically and virtually continuously photometrically quantitatively determined. In such case, a liquid sample is pumped to a photometric measuring area. On the way thereto, via another pump, a liquid reagent is introduced into the liquid sample stream, which leads to a color change of the liquid sample. The liquid sample is then photometrically examined.

For calibrating or adjusting the analytical devices employed in such a photometric method, standard solutions are used, which contain a predetermined concentration of the chemical substance. Disadvantageous in such case is that, especially in the case of non-linear concentration/signal relationships, a number of standard solutions are required for calibrating or adjusting the analytical device. In such case, depending on how high the concentration of the chemical substance in the liquid to be examined is, one of the standard solutions must be selected, which has a concentration of the chemical substance, which comes nearest to the concentration of the chemical substance in the liquid to be examined. The selected standard solution is then manually applied into the analytical device as a reference liquid. Then, the calibration or adjusting step is performed. The concentration of the chemical substance in the reference liquid measured during the calibration or adjusting step is compared with the concentration of this reference liquid known a priori. The selection and the manual exchanging of the reference liquid lead in running measurement process in process analytics to extended interruptions of the measurement process.

SUMMARY OF THE INVENTION

An object of the invention is thus to provide a method for calibrating and/or adjusting an analytical device for liquids, especially for aqueous solutions, in the case of which a calibrating and/or adjusting associated with the measurement process is possible without long interruptions of the measurement process.

The object is achieved according to the invention by features including that the predetermined concentration of the chemical substance in the reference liquid is gained by mixing at least two standard solutions, which contain different concentrations of the chemical substance. This has the advantage that the concentration of the chemical substance in the reference liquid can be very rapidly matched to the conditions reigning in the liquid to be examined. The desired concentration of the reference liquid is produced automatically during the calibration or adjusting procedure. Thus, it is always assured that the analytical device is adjusted for the right working point or working range. A preceding selection of the reference liquid is absent, as is a manual replacement of the required reference liquids, whereby the interruption of the measurement process by the calibration or adjusting procedure is reduced to a minimum. In order to make available as large a concentration range as possible, in which the concentration of the chemical substance can be gained via mixture of the two standard solutions, it is advantageous, when the concentrations of the standard solutions are markedly different from one another.

Advantageously, a first concentration of the chemical substance in the first standard solution lies near the lower limit of the measuring range of the analytical device, while the second standard solution has a second concentration of the chemical substance in the region of the upper limit of the measuring range. The first standard solution can, for example, have a concentration of 0% with reference to the measuring range (i.e. the analytical device measures in the pure standard solution a concentration of 0%), while the second standard solution contains a second concentration of such chemical substance of 100% with reference to the measuring range (i.e. the highest concentration still detectable by the analytical device, that is to say the "full scale deflection" of the device). The second standard solution can also be a saturated solution of the substance. Due to the different concentrations of the chemical substance in the standard solutions, any desired mixing ratios—and thus concentrations of the reference liquid—can be produced. A manual mixing, in such case, does not need to be done, since the mixing can be executed in a software driven manner, which represents an especially simple manner of proceeding.

In a variant, the predetermined concentration of the chemical substance in the reference liquid is ascertained from at least one measured value of concentration of a liquid to be examined, as measured in a preceding measurement. Based on the evaluation of measured values of concentration gained during the normal measurement process, the predetermined concentration of the reference liquid can be ascertained by auto-learning. In this way, the calibration or adjusting procedure is matched to the actually present conditions of the analytical process. Detailed preliminary investigations, which require a manual selection of the reference liquid, can be omitted in such case.

In a further development, the predetermined concentration of the reference liquid is determined from an average concentration value formed from a plurality of measured values of concentration for the liquid to be examined gained in preceding measurements. The formation of an average is the simplest method to determine the predetermined concentration of the reference liquid, since, thereby, the average conditions of the actual concentration of the chemical substance in the liquid to be examined are taken into consideration, from which an exact setting of the working point of the analytical device is possible.

In an embodiment, the wavelength of the light, with which the colored reference liquid and/or the colored liquid to be examined in the actual measurement process is irradiated, is selected as a function of the concentration of the chemical substance. Also this process occurs automatically via software, this representing an adaptive process.

In an additional variant, during an adjusting step of the analytical device, in the case of occurrence of a difference between the predetermined concentration and the measured concentration of the reference liquid, a correction value is determined, with which subsequent measured values of concentration for the chemical substance in the liquid to be examined are corrected. Due to this automatic self adjusting of the analytical device, highly accurate measured values of concentration for the liquid to be examined are gained during the on-going measurement process. The intervention of operating personnel is not necessary.

Advantageously, the calibrating and/or adjusting of the analytical device are performed as a function of time and/or as a function of event. The means that, in the on-going measurement process, a calibrating or adjusting of the analytical device occurs automatically, wherein the predetermined concentration of the reference liquid necessary therefore is determined by auto-learning from the gained measured values of concentration for the liquid to be examined. Via the repeated calibrating and adjusting, the reference liquid is continually changed, and thus automatically matches itself to the actual conditions in the liquid to be examined.

In an additional form of embodiment, the adjusting of the analytical device is performed when, as result of the calibrating of the analytical device, it is detected that the measured concentration of the chemical substance in the reference liquid exceeds a threshold value derived from the predetermined concentration. In this way, the point in time is prompt, at which a readjusting of the analytical device and thus also creation of the reference liquid with a new concentration of the chemical substance are introduced, so that the analytical device is adjusted to the right working point, and process analytics can always occur under the best preconditions.

BRIEF DESCRIPTION OF THE DRAWINGS

The invention lends itself to numerous forms of embodiment. One of these will now be explained in greater detail on the basis of the appended drawing, the sole FIGURE of which shows as follows:

FIG. 1 is a schematic representation of an analytical device for determining concentration of a chemical substance in an aqueous solution.

DETAILED DISCUSSION IN CONJUNCTION WITH THE DRAWINGS

FIG. 1 shows schematically an analytical device 1. From a liquid to be examined 2, the analytical device 1 withdraws a sample, which is fed via a line 3 and a line 6 to a sample chamber 7. Line 3 is, in such case, connected with a valve 4, which is opened and closed by a measuring electronics 10. A first pump 5, likewise mounted in line 3, moves the liquid to be examined 2 emerging from the opened valve 4 via line 6 to sample chamber 7 of analytical device 1.

Connected to line 6 are additionally two other lines 8 and 9. Line 8 extends into a reservoir containing a standard solution 11 composed of water and containing no chemical substance. Line 8 is connected to a second valve 12, which likewise is opened and closed as a function of signals from the measuring electronics 10. According to need, a pump 13 feeds the standard solution 11 flowing from the opened valve 12 into line 6 and, thus, into sample chamber 7.

A second standard solution 14, which contains the chemical substance in an amount equivalent to 100% of the measuring range, is brought via line 9 containing a third valve 15 and a third pump 16 likewise to line 6, and thus to sample chamber 7 of analytical device 1. The pumps 5, 13 and 16 are operated synchronously with the valves 4, 12 and 15 by the measuring electronics 10.

Moreover, sample chamber 7 includes a discharge line 17, in which a further valve 18 is arranged.

To determine the concentration of the chemical substance in the liquid to be examined located in the sample chamber 7, a light source 19 is provided, which irradiates the light-transmissive sample chamber 7 with light of a predetermined wavelength. A photodetector 20 arranged behind the sample chamber 7 measures the intensity of the light, and conveys an electrical signal corresponding to the intensity of the light to the measuring electronics 10, which includes a memory 21.

In the following, by way of example, phosphate, which frequently occurs in waste waters from dish washing machines, is considered as a chemical substance in the liquid to be examined 2. The second standard solution 14, in this case, contains phosphate in an amount equivalent to 100% of the measuring range of.

During a normal measurement process, n samples of the liquid to be examined 2 containing phosphate are measured. For each measurement, valve 4 is opened, and a sample of liquid to be examined 2 is pumped into sample chamber 7 via first pump 5. Valve 4 is then closed. Valves 12 and 15 remain unopened during this procedure. Into the liquid to be examined 2 are mixed two reagents in the form an ascorbic acid solution and a molybdate antimony oxide tartrate solution. Due to the mixing in of these reagents, the sample of liquid to be examined 2 turns blue. This happens because of absorption of a broad remainder of the spectral range of visible light, up to the near infrared region. The broad spectral range enables a large selection of emission wavelengths for phosphate analysis. For very low phosphate concentrations, a wavelength is selected, which lies in the vicinity of the absorption maximum (IR), while for high phosphate concentrations, green light, for example, is an option. Corresponding to the phosphate concentration of the liquid to be examined 2 contained in sample chamber 7, via measuring electronics 10, a wavelength of the light is determined, which is transmitted from the light source 19 to sample chamber 7 during the measurement process. The light transmitted with the predetermined wavelength is partially absorbed in sample chamber 7. The reduced intensity of the light leaving the sample chamber 7 is measured by the photodetector 20, wherein photodetector 20 transmits a corresponding electrical signal to measuring electronics 10. From the difference between the intensities of the light before entry into sample chamber 7 and after exit from sample chamber 7, via measuring electronics 10, the absorption of the light is determined. Thereafter, the measuring electronics 10 withdraws from its memory 21—which contains a relationship between the degree of absorption of the light and the concentration of phosphate in the liquid to be examined 2—the value, corresponding to the measured degree of absorption, for the phosphate concentration, which is contained in the investigated sample of the liquid to be examined. The concentration value for the liquid to be examined determined in this manner is stored in the memory 21. Then, the sample of the liquid to be examined, which is contained in sample chamber 7, is removed from sample chamber 7 via valve 18.

After, in the normal measurement process, n samples of the same type have been examined, an adjusting step of the analytical device 1 is performed. For this purpose, valve 4 is closed, and the liquid to be examined 2 located in sample chamber 7 is transferred out via the opened valve 18, so that an empty sample chamber 7 is available for the adjusting process. Valve 18 is then closed. From the stored n measured values of concentration, which were gained during the normal measurement process for the liquid to be examined, measuring electronics 10 determines an average concentration value for the chemical substance phosphate. Thereafter, a reference liquid with such an average concentration value is created. This occurs by the measuring electronics 10 activating the valves 12 and 15 in such a manner, that the standard solutions (water without phosphate) and 14 (100% of the phosphate measuring range of the analytical device) are metered into sample chamber 7 via the respective pumps 13 and 16 in such amounts that a reference liquid with the average concentration value of phosphate is made available in sample chamber 7. Since pumps 13, 16, which permit a highly accurate metering of the amounts of the two standard solutions 11 and 14, are used, the reference liquid can be provided very rapidly and without manual intervention.

Mixed into the produced reference liquid are two reagents in the form an ascorbic acid solution and a molybdate antimony oxide tartrate solution, and a color reaction is caused. Then, the transparent sample chamber 7 containing the reaction product made from reference liquid and reagents is irradiated with light of a certain wavelength, wherein the measuring electronics 10 has selected this wavelength in accordance with the average concentration value. Also, in the adjusting of the analytical device 1, the photodetector 20 measures the intensity of the light let through by the reference liquid. The measuring electronics 10, in turn, determines the ratio of the intensity (100%) of the light emitted by the light source 19, and the intensity, which photodetector 20 has measured. This quotient corresponds to the absorption of the light by the reference liquid with the predetermined average concentration value for the chemical substance phosphate. From the relationship between degree of absorption and measured concentration of the chemical substance phosphate stored in the memory 21, using the ascertained degree of absorption, the measured concentration of phosphate in the reference liquid is determined.

The measured reference concentration is then compared with the average concentration value, which was mixed from the standard solutions 11 and 14. If the concentration measured with the reference liquid agrees with the average concentration value, the analytical device 1 works in the right working range. If a difference occurs between the measured concentration and the average concentration value, from this difference, a correction factor is determined. In this way, the adjusting procedure is ended and the normal measurement process is continued, in the case of which, again, a number of m samples are taken one after the other from the reservoir of liquid to be examined 2 and filled into sample chamber 7, and are evaluated there with the described photometric method as regards absorption, wherein, from the degree of absorption, the concentration of the chemical substance in each of the m samples is again determined. Each of the m samples is corrected with the correction factor ascertained during the adjusting of the analytical device, whereby it is assured that always an exact determining of the concentration of the chemical substance, phosphate, in the liquid to be examined 2 is guaranteed. After determining the phosphate concentration in the m samples, a further adjusting step occurs, which proceeds in the exact same manner as the adjusting step explained earlier, only in such case, the measured m concentration values of the last measurement section are taken into consideration for determining the average concentration value for the reference liquid. In such case, via measuring electronics 10, the amounts of standard solutions 11 and 14 are newly determined, in order to produce a new average concentration value for the reference liquid.

Due to the described procedure, the concentration of the reference liquid needed for the calibration or adjusting procedure is adaptively matched to the contaminations currently reigning in the liquid to be examined 2, whereby the analytical device 1 always works in the right working point or working range. In this way, highly accurate measurements of the concentration of the chemical substance, which is contained in the liquid to be examined 2, are assured. The invention is not limited only to determining the concentration of phosphates, but can also be applied for a large number of other chemical substances.

The invention claimed is:

1. A method for calibrating and/or adjusting an analytical device for chemical substances in liquids, comprising the steps of:
    measuring with the analytical device a predetermined concentration of a chemical substance in a reference liquid by mixing the reference liquid with a reagent for producing a color change, followed by irradiating said reference liquid with light of a predetermined wavelength, and by determining said concentration based on absorption of the light by the reference liquid;
    comparing the measured concentration with the predetermined concentration of the chemical substance in the reference liquid; and
    calibrating and/or adjusting the analytical device based upon the comparison, wherein:
    the analytical device contains therein at least two standard solutions which contain different concentrations of the chemical substance, and the predetermined concentration of the chemical substance in the reference liquid is gained by automatically mixing in the analytical device selected amounts of the at least two standard solutions.

2. The method as claimed in claim 1, wherein:
    a first concentration of the chemical substance in a first standard solution amounts to 0%, and a second standard solution contains a second concentration of 100%, with reference to a measuring range of the analytical device for the same chemical substance; and
    a highest concentration detectable by the analytical device corresponds to a concentration of 100%.

3. The method as claimed in claim 1, wherein:
    the predetermined concentration of the chemical substance in the reference liquid is ascertained from at least one measured value of concentration of said chemical substance measured in a preceding measurement in a liquid to be examined, which is different from the reference liquid.

4. The method as claimed in claim 3, wherein:
    the predetermined concentration of the chemical substance in the reference liquid is determined from an average concentration value formed from a plurality of measured values of concentration of the chemical substance in the liquid to be examined gained in preceding measurements.

5. The method as claimed in claim 4, wherein:
    the predetermined concentration of the reference liquid is determined by auto-learning of the analytical device from the plurality of measured values of the concentration of the chemical substance in the liquid to be examined.

6. The method as claimed in claim 4, wherein:
the predetermined concentration of the chemical substance in the reference liquid is determined by measuring electronics of said analytical device.

7. The method as claimed in claim 3 wherein:
the wavelength of the light, with which the colored reference liquid is irradiated, is selected as a function of concentration of the chemical substance.

8. The method as claimed in claim 1, wherein:
for adjusting the analytical device, in the case of occurrence of a difference between the predetermined concentration and the measured concentration of the reference liquid, a correction value is determined, with which subsequent measured values of concentration of the chemical substance in a liquid to be examined are corrected.

9. The method as claimed in claim 8, wherein:
calibrating and/or adjusting of the analytical device are performed as a function of time.

10. The method as claimed in claim 8, wherein:
the adjusting of the analytical device is performed when, as result of calibrating of the analytical device by comparing the measured concentration with the predetermined concentration of the reference liquid it is detected that the measured concentration of the chemical substance in the reference liquid exceeds a threshold value derived from the predetermined concentration.

11. The method as claimed in claim 1, wherein:
said liquids and said reference liquid are aqueous solutions and the method is used in process analytics.

12. A method for calibrating and/or adjusting an analytical device for chemical substances in liquids, comprising the steps of:
measuring with the analytical device a predetermined concentration of a chemical substance in a reference liquid by mixing the reference liquid with a reagent for producing a color change, followed by irradiating said reference liquid with light of a predetermined wavelength, and by determining said concentration based on absorption of the light by the reference liquid;

comparing the measured concentration with the predetermined concentration of the chemical substance in the reference liquid; and calibrating and/or adjusting the analytical device based upon the comparison, wherein:

the analytical device contains therein at least two standard solutions which contain different concentrations of the chemical substance, and the predetermined concentration of the chemical substance in the reference liquid is gained by automatically mixing in the analytical device selected amounts of the at least two standard solutions; and the wavelength of the light, with which the colored reference liquid is irradiated, is selected as a function of concentration of the chemical substance; and the predetermined concentration of the chemical substance in the reference liquid is determined by measuring electronics of said analytical device.

13. The method as claimed in claim 12, wherein:
the predetermined concentration of the chemical substance in the reference liquid is determined from an average concentration value formed from a plurality of measured values of concentration of the chemical substance in a liquid to be examined gained in preceding measurements.

14. The method as claimed in claim 13, wherein:
the predetermined concentration of the chemical substance in the reference liquid is determined by measuring electronics of said analytical device and the reference liquid with said predetermined concentration is produced automatically by the analytical device.

* * * * *